United States Patent [19]

Stern

[11] Patent Number: 4,585,868

[45] Date of Patent: Apr. 29, 1986

[54] PRECURSORS OF 6,7-DIHYDRO-5,8-DIMETHYL-9-FLUORO-1-OXO-1H,5H-BENZO[IJ]QUINOLIZINE-2-CARBOXYLIC ACID

[75] Inventor: Richard M. Stern, Cottage Grove, Minn.

[73] Assignee: Riker Laboratories, Inc., St. Paul, Minn.

[21] Appl. No.: 624,408

[22] Filed: Jun. 25, 1984

Related U.S. Application Data

[62] Division of Ser. No. 441,245, Nov. 12, 1982, Pat. No. 4,472,405.

[51] Int. Cl.$^4$ .................. C07D 215/48; C07D 215/14
[52] U.S. Cl. ..................... 546/165; 546/170; 546/180
[58] Field of Search ................. 546/165, 180, 170

[56] References Cited

U.S. PATENT DOCUMENTS

| | | | |
|---|---|---|---|
| 3,896,131 | 7/1975 | Gerster | 546/94 |
| 4,036,963 | 7/1977 | Gialdi et al. | 546/170 |
| 4,301,288 | 11/1981 | Leir et al. | 546/94 |

FOREIGN PATENT DOCUMENTS

| | | | |
|---|---|---|---|
| 1186777 | 4/1970 | Fed. Rep. of Germany | 546/165 |
| 1901290 | 8/1970 | Fed. Rep. of Germany | 546/165 |
| 6128762 | 10/1981 | Japan | 546/180 |

OTHER PUBLICATIONS

Acheson, et al. "Add'n Rxs of heterocyclic" CA 82: 154773j, 1975.
Otsuka Pharm. "5 6–Dihalo–2–alkylquinolines" CA 96: 19987f.
Chernuk et al. "Synthesis & properties of . . . " CA 83: 179223p.
Gyul'budagyan, L. V. et al, "2,5–dimethyl–2H, 3 4–dihydrothiopyrano[3,2]-quinolines. CA 87: 167919q.

*Primary Examiner*—Richard A. Schwartz
*Attorney, Agent, or Firm*—Donald M. Sell; James A. Smith; Robert W. Sprague

[57] ABSTRACT

The compounds 5-carboxyl-6-fluoroquinaldine, 6-fluoro-5-methylquinaldine, 6-fluoro-5-methyl-1,2,3,4-tetrahydroquinaldine, 1,2-dihydro-6-fluoro-5-hydroxymethylquinaldine and diethyl 2-[N-(6-fluoro-5-methyl-1,2,3,4-tetrahydroquinaldinyl)]methylenemalonate are disclosed as useful intermediates for preparing the antimicrobial agent 6,7-dihydro-5,8-dimethyl-9-fluoro-1-oxo-1H,5H-benzol[ij]quinolizine-2-carboxylic acid.

4 Claims, No Drawings

PRECURSORS OF 6,7-DIHYDRO-5,8-DIMETHYL-9-FLUORO-1-OXO-1H,5H-BENZO[IJ]QUINOLIZINE-2-CARBOXYLIC ACID

This is a division of application Ser. No. 441,245 filed Nov. 12, 1982, now U.S. Pat. No. 4,472,405.

TECHNICAL FIELD

This invention relates to derivatives of the heterocyclic system known as benzo[ij]quinolizine. More particularly, it relates to 8-substituted 6,7-dihydro-5-methyl-9-fluoro-1-oxo-1H,5H-benzo[ij]quinolizine-2-carboxylic acid and derivatives thereof. The use of the compounds of the invention as antimicrobial agents, pharmaceutical compositions containing the compounds and intermediates for the preparation of the compounds are also included within the scope of the invention.

BACKGROUND OF THE INVENTION

U.S. Pat. No. 3,896,131 describes a broad class of 6,7-dihydro-5-methyl-1-oxo-1H,5H-benzo[ij]quinolizine-2-carboxylic acids as antimicrobial agents. The patent specifically discloses several compounds substituted by halogen and/or methyl on the benzo ring. The compound 6,7-dihydro-9-fluoro-5-methyl-1-oxo-1H,5H-benzo[ij]-quinolizine-2-carboxylic acid (now known as flumequine) which is disclosed in the aforementioned patent has received the most attention for its antimicrobial activity. It has now been found that the corresponding novel 8-methyl-9-fluoro compound exhibits greatly enhanced antimicrobial activity.

U.S. Pat. No. 4,301,289 describes the compounds 6-fluoroquinaldine, 6-fluoro-1,2,3,4-tetrahydroquinaldine, and dialkyl 2-[N-(6-fluoro-1,2,3,4-tetrahydroquinaldinyl]- methylenemalonates.

DESCRIPTION OF THE INVENTION

The present invention relates to the compound 6,7-dihydro-5,8-dimethyl-9-fluoro-1-oxo-1H,5H-benzo[ij]-quinolizine-2-carboxylic acid and its carboxylate derivatives. This invention also relates to the pharmacological use of these compounds as antibiotics and to pharmaceutical compositions comprising these compounds. The invention also relates to synthetic intermediates useful for preparing these compounds.

Specifically, this invention relates to the novel compound 6,7-dihydro-5,8-dimethyl-9-fluoro-1-oxo-1H,5H-benzo[ij]quinolizine-2-carboxylic acid of Formula I

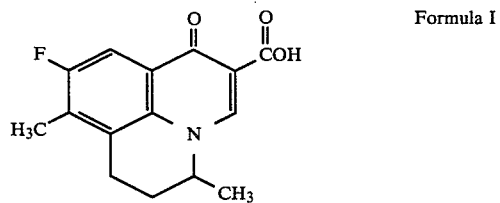

Formula I or a pharmaceutically acceptable carboxylate salt thereof. These compounds are useful antimicrobials.

Compounds of the invention have an optically active carbon at the 5 position. All such optical isomers are included within the scope of the invention.

It is well known to the art that pharmaceutically acceptable salts such as alkali metal, alkaline earth, aluminum, iron, silver and other metal and amine salts of pharmaceutically active acids are the equivalents of the acids in terms of activity, and in some cases may even offer advantages in absorption, formulation and the like. Pharmaceutically-acceptable carboxylate salts of the free acid compounds of the invention are readily prepared by reaction of the acid with a base and subsequent evaporation to dryness. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in a selected solvent.

Other useful derivatives of the compound of the invention include the acyl chloride, esters and alkylaminoalkyl ester salts thereof. In the acyl chloride derivative, the hydroxyl portion of the carboxylic acid group is removed and replaced with chlorine. In the ester derivatives, the hydrogen portion of the carboxylic acid group is replaced with an alkyl or substituted alkyl, preferably an alkylaminoalkyl group.

Esters and the acyl chloride of the compound of the invention may be obtained as intermediates during the preparation of the acidic compound. In some cases, the esters may be prepared directly using standard synthetic methods. These esters and the acyl chloride exhibit antimicrobial activity, but they are primarily of interest as synthetic intermediates, although in some instances hydrolyzable or salt-forming esters may be of interest as therapeutic agents. Preferred esters are alkyl esters and alkylaminoalkyl esters having one to four carbon atoms in the alkyl group. Especially preferred are alkylaminoalkyl esters such as the dimethylaminoethyl esters which will form salts, e.g., hydrochlorides.

Ester derivatives are readily prepared by reacting the free acid of Formula I with thionyl chloride to provide the novel acyl chloride derivative. The acyl chloride is reacted with the appropriate alcohol to provide the desired ester.

The antimicrobial activity of the compounds of the present invention can be demonstrated by the known, standard plate dilution method for bacterial susceptibility testing of fastidious microorganisms towards antibiotics, sulfonamides and other chemotherapeutic agents. Tryptone soy agar (oxoid) of the following composition is the culture medium.

Oxoid tryptone: 15 g.
Oxoid soy peptone: 2 g.
Sodium chloride: 5 g.
Oxoid agar-agar No. 3: 15 g.
Water: 1 liter Using this test, compounds of the invention have been found to have a broad spectrum of activity against gram-positive and gram-negative microorganisms.

The compounds of the invention are active against microorganisms either in the absence or presence of 10 percent horse serum.

The test procedure used to determine activity as employed in connection with the present invention provides information on the amount of a compound which gives complete inhibition, partial inhibition or no inhibition of microbial growth on the agar plates. In the tests, the selected compound is added to the agar medium to give concentrations of zero, one, ten and one hundred milligrams per liter. A series of plates with these concentrations is prepared. Ten percent horse serum is added to one series of such plates. Aliquots of broth culture of any of twelve species of microorganisms are innoculated onto the agar plates containing the various compound concentrations. The plates are incubated at 37° C. in a 10 percent carbon dioxide atmosphere for 18-24 hours. The microbial growth on each plate is read visually, and minimum inhibitory concentrations (for partial or complete inhibition) are recorded. Some of the microorganisms which are used for this test are:

1. *Staphylococcus aureus*
2. *Bacillus subtilis*
3. *Escherichia coli*
4. *Pseudomonas aeruginosa*
5. *Streptococcus sp.* *
6. *Aspergillus niger*
7. *Candida albicans*
8. *Acinetobacter lwoffi*
9. *Acinetobacter anitratum*
10. *Klebsiella pneumoniae*
11. *Streptococcus fecaelis*
12. *Serratia marcescens*

*Strains isolated from dental caries in rats or hamsters at the National Institute of Dental Health and grown in PFY or APT agar.

The compounds of the invention possess antimicrobial activity towards one or more of the above microorganisms. Of specific significance is the high level of activity of the compound of formula I and its salts against Pseudomonas aeruginosa, a particularly bothersome species associated with many topical infections. This type of activity is very unusual in benzoquinolizine-type antibacterials.

It will be understood by those skilled in the art that the species used are representative indicator species, as it would be impractical to screen against all bacteria. It is well known in the art that broad spectrum activity can be predicted on the basis of activity shown against selected representative bacterial species.

The compounds of the invention are active when administered orally to animals. They are excreted in the urine, and are effective urinary tract antibacterials in mammals. They may also be used in the treatment of pulmonary infections, soft tissue infections, burn infections and bacteremias.

Compounds of the invention are active against microorganisms in vitro or topically. In vitro activity is useful in itself, since antimicrobial agents may be used for disinfecting and sterilizing, e.g., medical and dental equipment, as components of disinfecting solutions.

The acute oral toxicity of the compounds of the invention generally is moderate to low compared with the effective oral dose, and they have an acceptable therapeutic ratio ($LD_{50}/ED_{50}$) of greater than 80.

The acidic compound of the invention is a white crystalline material when purified. It is substantially insoluble in water, lower alcohols or hydrocarbons and is more soluble in halogenated solvents, N,N-dimethylformamide and the like. The salts, especially the alkali metal salts, have appreciable solubility in water and lower alcohols.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of a compound used to treat, for example, a microbial urinary infection by oral administration will be an effective amount less than a toxic amount. The amount to be administered to control an infection will depend on the species, sex, weight, physical condition and many other factors, but this judgment is well within the skill of the medical art. Usually the amount will be less than 100 mg/kg per dose. Conveniently this is administered in the form of the usual pharmaceutical preparations such as capsules, tablets, emulsions, solutions and the like. Excipients, fillers, coatings, etc. are employed with tablets or capsules, as is well known in the art.

It is known to the art that antimicrobial agents are used as growth promoters in various animal and bird species. Although not yet verified, it is inferred from their outstanding antimicrobial activity that the compounds of the invention can be used for this purpose also. The compounds of the invention may also be used for the control of microbial (e.g., Erwinia amylovora) infections of plants, e.g., by spraying or dusting a formulation of these compounds on the affected area.

The acid compound of the invention may be prepared as described in the following reaction scheme:

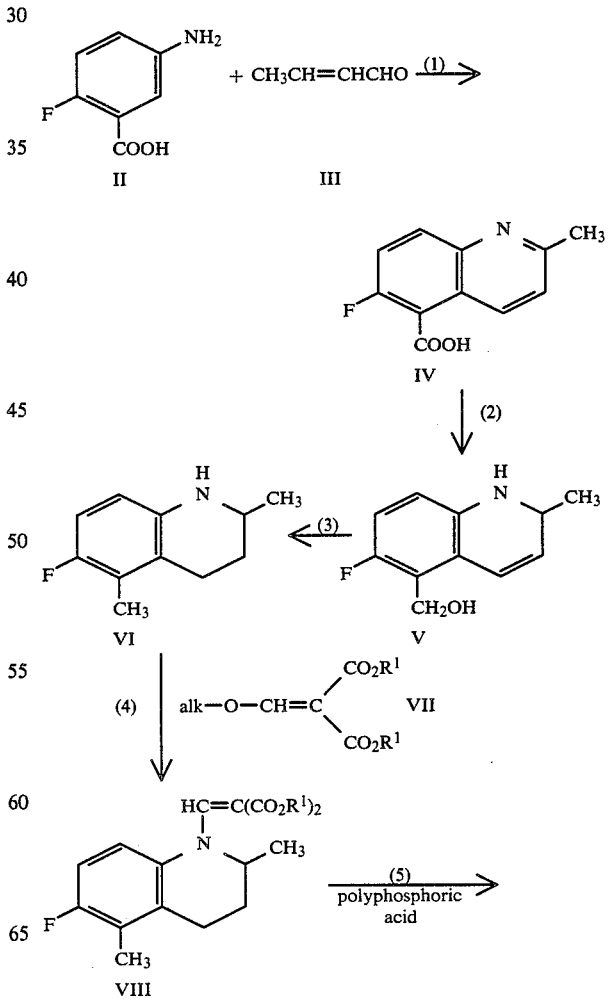

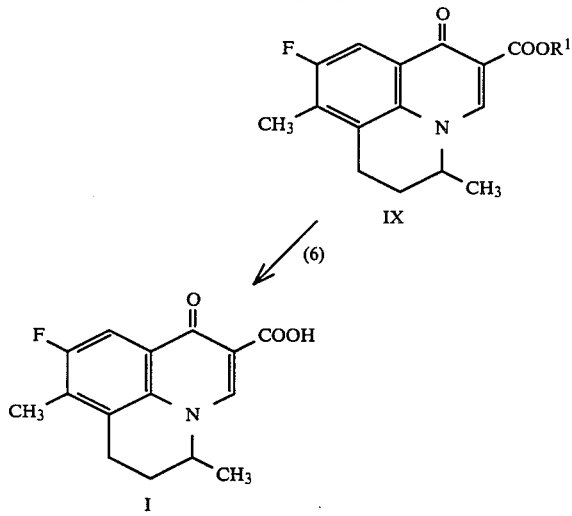

wherein alk and each $R^1$ are independently alkyl groups containing 1 to about 4 carbon atoms, and preferably 1 to 2 carbon atoms.

In the first step of the reaction scheme, 5-amino-2-fluorobenzoic acid of Formula II is reacted with illustrated crotonaldehyde of Formula III or a precursor of crotonaldehyde which generates crotonaldehyde under the acidic conditions of the reaction. Suitable precursors of crotonaldehyde which may be used in Step (1) include acetaldehyde, acetal or paraldehyde. The product of step (1) is the novel compound 5-carboxy-6-fluoroquinaldine of Formula IV. The reaction is conducted in the presence of a dilute aqueous acid such as sulfuric acid or hydrochloric acid, hydrochloric acid being preferred. The reaction is conducted at a temperature between about 50° C. and the reflux temperature of the reaction mixture. It is advantageous to conduct the reaction in the presence of a reagent pair consisting of a weak oxidizing agent and a weak reducing agent. Suitable oxidizing agents include alkali metal or alkaline earth salts of the organic acid meta-nitrobenzenesulfonic acid. The sodium and potassium salts are preferred. The free acids may also be used as oxidizing agents. Suitable reducing agents include ferrous sulfate, ferric sulfate, ferric chloride and the like. The presently preferred reagent pair is the sodium salt of m-nitrobenzenesulfonic acid as the oxidizing agent and ferrous sulfate as the reducing agent. Employment of at least about theoretical amounts of the oxidizing agent and reducing agent (i.e., at least 0.25 mole of each per mole of the aminobenzoic acid of Formula II) is preferred. If catalytic amounts of the reducing agent are used, the reaction proceeds, but at a slower rate.

Steps (2) and (3) of the reaction scheme involve reduction of the carboxyl group of the intermediate of Formula IV. The intermediate of Formula IV is reduced in step (2) to provide the novel intermediate 1,2-dihydro-6-fluoro-5-hydroxymethylquinaldine of Formula V. This reduction is carried out using diborane in a suitable solvent such as tetrahydrofuran. The mixture is heated at reflux for several hours.

In step (3), the 1,2-dihydro-6-fluoro-5-hydroxymethylquinaldine of Formula V is reduced to provide the novel intermediate 6-fluoro-5-methyl-1,2,3,4-tetrahydroquinaldine of Formula VI. This reduction is carried out using hydrogen gas and a mixture of palladium on charcoal and platinum on charcoal. Alternatively, the reduction may be accomplished in two sequential steps, the first step involving the use of one catalyst and the second the other. In either case, the reduction is carried out in a solvent such as ethanol, using a Paar apparatus.

The 6-fluoro-5-methyl-1,2,3,4-tetrahydroquinaldine of Formula VI is condensed with a dialkyl alkoxymethylenemalonate of Formula VII in step (4). The preferred dialkyl alkoxymethylenemalonate is diethyl ethoxymethylenemalonate since it is most readily available. The condensation reaction requires heating of the reactants until the reaction is complete as determined by chromatographic analysis. The reaction is conducted in the absence of solvent at a temperature of 100 to 200° C. for several hours. It is preferred that the reaction be conducted at a temperature of 140°–150° C. for two hours. Alternatively, the reaction may be conducted in the presence of an inert organic solvent which forms an azeotropic mixture with the alcohol formed upon condensation of the dialkyl alkoxymethylenemalonate (e.g., ethanol where diethyl ethoxymethylenemalonate is employed in step (4)). The reaction mixture is heated at its reflux temperature and the azeotropic mixture comprising the alcohol and the organic solvent is collected, for example, in a Dean Stark trap. Fresh organic solvent is generally added to the reaction mixture as the solvent is depleted during distillation. Removal of the alcohol from the reaction mixture drives the condensation reaction to substantial completion and increases the yield. The product of step (4) is the novel intermediate of Formula VIII. This intermediate may be isolated, e.g., as an oil or a solid, or the product of step (4) may be used directly in step (5) below without isolation of the intermediate.

In step (5) the intermediate of Formula VIII is cyclized to form the ester of Formula IX. The cyclization step is carried out by heating the intermediate of Formula VIII in the presence of polyphosphoric acid. The temperature of the reaction is preferably 150°–160° C. Alternatively, cyclization of the intermediate of Formula VIII is carried out in the presence of phosphorus oxychloride by refluxing for several hours, evaporating excess phosphorus oxychloride and refluxing in the presence of water.

The ester of Formula IX is saponified in step (6) by conventional means to provide 6,7-dihydro-5,8-dimethyl-9-fluoro-1-oxo-1H,5H-benzo[ij]quinolizine-2-carboxylic acid of Formula I.

The following examples are provided to illustrate the synthetic methods useful to obtain compounds of the invention, and are not intended to be limiting of the invention.

EXAMPLE 1

Part A. Preparation of 5-carboxyl-6-fluoroquinaldine

A mixture of 95.2 g of 5-amino-2-fluorobenzoic acid (0.60 moles), 74.3 g (0.33 mole) of sodium meta-nitrobenzenesulfonate, 46.2 g (0.17 mole) of ferrous sulfate heptahydrate and 660 ml of 9N hydrochloric acid was heated to 90°–95° C. Crotonaldehyde (96%), 77 g (1.0 mole), was added dropwise over 2.5 hours with vigorous stirring, the temperature being maintained just below the reflux temperature. After stirring an additional half hour, the hot solution was filtered through a glass wool plug. The filtrate was cooled to 30° C., treated with decolorizing charcoal, and filtered. The clear filtrate was cooled on ice with stirring to provide a yellow solid. The solid was separated by filtration, washed with acetone, and dried. The solid was then dissoved in 400 ml of hot water, and a solution of 50 g of sodium acetate in 100 ml of water was added thereto. The product was 58.2 g of cream crystals of 5-carboxyl-6-fluoroquinaldine. The structural assignment was confirmed by infrared and nuclear magnetic resonance spectral analyses.

EXAMPLE 2

Preparation of the Novel Intermediate 1,2-dihydro-6-fluoro5-hydroxymethylquinaldine To a stirred slurry of 20.0 g (97.6 mmole) of 5-carboxyl-6-fluoroquinaldine in 400 ml of tetrahydrofuran was added dropwise 300 ml of lM diborane in tetrahydrofuran (0.3 mole). The solution was stirred at 20° C. for one hour, heated at its reflux temperature for two hours and then allowed to cool. A mixture of 150 ml of water and 100 ml of tetrahydrofuran was added, and the mixture was stirred for 30 minutes on a steam bath and cooled. The aqueous layer was saturated with potassium carbonate by stepwise addition of the salt. The organic layer was separated and the aqueous layer was extracted with 200 ml of diethyl ether. The extracts were combined with the organic layer and dried over magnesium sulfate. Evaporation of the solvent provided an oil which was dissolved in a solution of 400 ml of ethanol and 15 ml of concentrated hydrochloric acid. After heating this mixture at reflux for one hour, the solvent was evaporated to provide a solid. The solid was dissolved in 200 ml of water, and the solution was basified with aqueous sodium hydroxide to provide a solid which was chiefly 1,2-dihydro-6-fluoro-5-hydroxymethylquinaldine as determined by nuclear magnetic resonance spectral analysis. Other isomers were also present.

EXAMPLE 3

Preparation of Novel Intermediate 6-Fluoro-5-methyl-1,2,3,4-tetrahydroquinaldine A solid which was chiefly 1,2-dihydro-6-fluoro-5-hydroxymethylquinaldine (13.2 g) prepared according to Example 2 was dissolved in 300 ml of ethanol and 10 ml of concentrated hydrochloric acid. To this solution was added 1 g of 5% platinum on charcoal and 3 g of 5% palladium on charcoal. The solution was hydrogenated at 50 psi at about 20° C. on a Paar apparatus. After absorption of about 12 psi of hydrogen (the theoretical amount needed), the solution was filtered and the solvent was removed by evaporation to provide a solid. Nuclear magnetic resonance spectral analysis showed slightly incomplete reduction. Therefore the solid was dissolved in 300 ml of aqueous (95%) ethanol to which 2 g of platinum on charcoal was added, and the solution was hydrogenated at 50 psi on the Paar apparatus for about 16 hours. The solution was then filtered and the solvent was evaporated. The solid recovered was dissolved in 50 ml of water. This solution was basified with aqueous sodium hydroxide and then extracted with diethyl ether. Evaporation of the ether provided 6-fluoro-5-methyl-1,2,3,4-tetrahydroquinaldine as an oil.

EXAMPLE 4

Alternative Preparation of 6-Fluoro-5-methyl-1,2,3,4-tetrahydroquinaldine

A solid which was chiefly 1,2-dihydro-6-fluoro-5-hydroxymethylquinaldine (7.0 g) was dissolved in 200 ml of ethanol containing 1 ml of concentrated hydrochloric acid, 1.0 g of 5% palladium on charcoal, and 1.0 g 5% platinum on charcoal and the mixture was hydrogenated at 50 psi at 20° C. for 5 hours. The solution was filtered and the filtrate was evaporated to provide white solid 6-fluoro-5-hydroxy-methyl-1,2,3,4-tetrahydroquinaldine as determined by nuclear magnetic resonance spectral analysis.

The solid was dissolved in 350 ml of ethanol containing 3 ml of concentrated hydrochloric acid and 3.0 g of palladium on charcoal and was hydrogenated at 50 psi overnight. The mixture was filtered, and the filtrate was evaporated to provide white solid 6-fluoro-5 -methyl-1,2,3,4-tetrahydroquinaldine hydrochloride. The free base was separated by dissolving the solid in water, basifying with 10% aqueous sodium hydroxide solution, extracting into diethyl ether and evaporating the ether to provide a yellow solid.

EXAMPLE 5

A mixture of 9.3 g of 6-fluoro-5-methyl-1,2,3,4-tetrahydroquinaldine and 17 ml of diethyl ethoxymethylenemalonate was heated at 150°–160° C. for 3.5 hours, and then cooled to 100° C. To this solution was added 56 g of polyphosphoric acid, and the mixture was stirred for one hour while heating on a steam bath. The mixture was then cooled to room temperature and allowed to stand for about 72 hours. To this mixture, containing ethyl 1,2-dihydro-5,8-dimethyl-9-fluoro-1-oxo-1H,5H-benzo[ij]quinolizine-2-carboxylate, was added 250 ml of 20% aqueous sodium hydroxide to make the solution basic. The solution was then heated at its reflux temperature for 2 hours, cooled, and acidified with concentrated hydrochloric acid. The solid was separated by filtration and recrystallized from aqueous N,N-dimethylformamide. Washing with ethanol followed by drying provided 6,7-dihydro-5,8-dimethyl-9-fluoro-1-oxo-1H,5H-benzo[ij]quinolizine-2-carboxylic acid as an off-white solid, m.p. 269-272° C. Analysis: Calculated for $C_{15}H_{14}FNO_3$: %C, 65.4; %H, 5.1; %N, 5.1; Found: %C, 65.0; %H, 5.0; %N, 5.0.

EXAMPLE 6

The antibacterial activity of the free acid compound of the present invention and that of several 6,7-dihydro-5-methyl-1-oxo-1H,5H-benzo[ij]quinolizine-2-carboxylic acids of the prior art was determined using the standard plate dilution method described hereinabove. The tests were run both in the absence (Column A) and in the presence (Column B) of horse serum as described hereinabove and amounts of the antimicrobial agent were as indicated. The results (recorded at the minimum concentrations in milligrams of the active antimicrobial agent per liter which provide partial or complete inhibition of the growth of the indicated microorganisms) are shown in the table below:

| COMPOUND | STREPTOCOCCUS SPECIES | | STAPHYLOCOCCUS AUREUS | | ESCHERICIA COLI | | PSEUDOMONAS AERUGINOSA | |
| --- | --- | --- | --- | --- | --- | --- | --- | --- |
| | A | B | A | B | A | B | A | B |
| 6,7-dihydro-5,8-dimethyl-9-fluoro-1- | 10 | 10 | 0.1* | 0.1* | 0.1 | 0.1 | 10 | 10 |

-continued

| COMPOUND | STREPTOCOCCUS SPECIES | | STAPHYLOCOCCUS AUREUS | | ESCHERICIA COLI | | PSEUDOMONAS AERUGINOSA | |
|---|---|---|---|---|---|---|---|---|
| | A | B | A | B | A | B | A | B |
| oxo-1H,5H—benzo[ij]quinolizine-2-carboxylic acid | | | | | | | | |
| 6,7-dihydro-9-fluro-5-methyl-1-oxo-1H,5H—benzo[ij]quinolizine-2-carboxylic acid | 100 | 100 | 10 | 10 | 1 | 1 | 100 | 100 |
| 6,7-dihydro-5,8-dimethyl-1-oxo-1H,5H—benzo[ij]-quinolizine-2-carboxylic acid | 100 | 100 | 1 | 1 | 1 | 1 | 100 | 100 |
| 6,7-dihydro-5,8,10-trimethyl-1-oxo-1H,5H—benzo-[ij]quinolizine-2-carboxylic acid | 100 | 100 | 1 | 1 | 1 | 1 | 100 | 100 |
| 6,7-dihydro-5,9-dimethyl-1-oxo-1H,5H—benzo[ij]quinoline-2-carboxylic acid | 100 | 100 | 100 | 100 | 10 | 10 | >100 | >100 |
| 6,7-dihydor-5,10-dimethyl-1-oxo-1H,5H—benzo[ij]quinolizine-2-carboxylic acid | 100 | 100 | 100 | 100 | 10 | 100 | >100 | >100 |

*partial inhibition

It is seen that the compound of the present invention exhibits significantly greater activity than the compounds of the prior art.

EXAMPLE 7

To a solution of 0.17 g (4.25 mmole) of sodium hydroxide in 75 ml of water was added 1.3 g (4.73 mmole) of 1,2-dihydro-5,8-dimethyl-9-fluoro-1-oxo-1H,5H-benzo[ij]- quinolizine-2-carboxylic acid. The mixture was stirred for about 30 minutes and undissolved acid was removed by filtration. The solution was lyophilized to provide 1.1 g of white fluffy solid sodium 1,2-dihydro-5,8-dimethyl-9-fluoro-1-oxo-1H,5H-benzo[ij]quinolizine-2-carboxylate. Analysis: Calculated for $C_{15}H_{13}FNO_3Na \cdot 0.5H_2O$: %C, 58.8; %H, 4.6 %N, 4.6; Found: %C, 58.9; %H, 4.6; %N, 4.4.

What is claimed is:

1. The compound 5-carboxyl-6-fluoroquinaldine.
2. The compound 6-fluoro-5-methyl-1,2,3,4,-tetrahydroquinaldine.
3. The compound 1,2-dihydro-6-fluoro-5-hydroxymethylquinaldine.
4. The compound diethyl 2-[N-(6-fluoro-5-methyl-1,2,3,4-tetrahydroquinaldinyl)]methylenemalonate.

* * * * *